US009168112B2

(12) United States Patent
Haber

(10) Patent No.: US 9,168,112 B2
(45) Date of Patent: *Oct. 27, 2015

(54) MULTI-LAYER SURGICAL GUIDE

(71) Applicant: Guided Surgery Solutions, LLC, Wellesley, MA (US)

(72) Inventor: Jerome Haber, Weston, MA (US)

(73) Assignee: Guided Surgery Solutions, LLC, Wellesley, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/167,678

(22) Filed: Jan. 29, 2014

(65) Prior Publication Data

US 2014/0203463 A1   Jul. 24, 2014

Related U.S. Application Data

(63) Continuation-in-part of application No. 13/951,818, filed on Jul. 26, 2013.

(60) Provisional application No. 61/676,734, filed on Jul. 27, 2012, provisional application No. 61/811,690, filed on Apr. 12, 2013.

(51) Int. Cl.
*A61C 8/00* (2006.01)
*A61B 6/03* (2006.01)
*A61B 6/14* (2006.01)
*A61B 6/00* (2006.01)
*A61C 1/08* (2006.01)
(Continued)

(52) U.S. Cl.
CPC ............... *A61C 8/0089* (2013.01); *A61B 6/032* (2013.01); *A61B 6/14* (2013.01); *A61B 6/4085* (2013.01); *A61C 1/084* (2013.01); *A61C 13/0013* (2013.01); *A61C 9/0053* (2013.01); *A61C 13/0004* (2013.01)

(58) Field of Classification Search
CPC ...... A61C 8/009; A61C 8/0089; A61C 1/084; A61C 13/0013; A61C 9/0053; A61C 13/004; A61B 6/032; A61B 6/14; A61B 6/4085
USPC .................................................... 433/75, 76
See application file for complete search history.

(56) References Cited

U.S. PATENT DOCUMENTS 6,814,575 B2 * 11/2004 Poirier ............................ 433/75
7,044,735 B2 *  5/2006 Malin ............................. 433/75
7,331,786 B2 *  2/2008 Poirier ............................ 433/75

(Continued)

FOREIGN PATENT DOCUMENTS

EP         2 425 797 A1 *  3/2012
EP         2425797            3/2012
WO     WO-2014018829         1/2014

OTHER PUBLICATIONS

"International Application Serial No. PCT/US13/52191, Search Report and Written Opinion mailed Jan. 15, 2014", 18 pages.

(Continued)

*Primary Examiner* — Ralph Lewis
(74) *Attorney, Agent, or Firm* — Strategic Patents, P.C.

(57) ABSTRACT

A drill guide employs multiple layers of materials with different mechanical properties in order to achieve concurrent goals of rigidity, fit and retention. For example, a rigid exterior shell and a soft interior may be used together to securely and precisely fit a drill guide to a surgical site.

20 Claims, 13 Drawing Sheets

(51) Int. Cl.
*A61C 9/00* (2006.01)
*A61C 13/00* (2006.01)

(56) References Cited

U.S. PATENT DOCUMENTS

| | | | |
|---|---|---|---|
| 7,845,943 B2* | 12/2010 | Meitner | 433/75 |
| 8,135,492 B2* | 3/2012 | Yau et al. | 700/182 |
| 2004/0115586 A1 | 6/2004 | Andreiko et al. | |
| 2009/0136902 A1* | 5/2009 | Zundorf et al. | 433/223 |
| 2009/0287332 A1 | 11/2009 | Adusumilli et al. | |
| 2010/0004698 A1 | 1/2010 | De Moyer | |
| 2010/0105010 A1* | 4/2010 | Mah | 433/215 |
| 2010/0240000 A1* | 9/2010 | Yau et al. | 433/37 |
| 2010/0255445 A1 | 10/2010 | Gantes | |
| 2011/0311941 A1* | 12/2011 | Yi et al. | 433/75 |
| 2012/0135373 A1* | 5/2012 | Cheng et al. | 433/75 |
| 2013/0065195 A1* | 3/2013 | De Clerck | 433/29 |
| 2013/0071811 A1* | 3/2013 | Groscurth et al. | 433/75 |
| 2013/0144422 A1* | 6/2013 | Choi et al. | 700/119 |
| 2014/0026419 A1 | 1/2014 | Haber | |
| 2014/0162213 A1 | 6/2014 | Haber | |

OTHER PUBLICATIONS

"U.S. Appl. No. 13/951,818, Non-Final Office Action mailed Jun. 12, 2014", 13 pages.

"U.S. Appl. No. 13/951,818, Notice of Allowance mailed Apr. 10, 2015", 7 pages.

* cited by examiner

MULTI-LAYER SURGICAL GUIDE

RELATED APPLICATIONS

This application is a continuation-in-part of U.S. application Ser. No. 13/951,818 filed on Jul. 26, 2013, which claims the benefit under 35 U.S.C. §119(e) of U.S. application Ser. No. 61/676,734 filed on Jul. 27, 2012 and U.S. App. No. 61/811,690 filed on Apr. 12, 2013. The entire content of each of these applications is hereby incorporated by reference.

This application is related to U.S. application Ser. No. 12/816,710, the entire content of which is hereby incorporated by reference.

BACKGROUND

The invention relates to composite dental drill guides for use in restorative dental surgery and similar procedures.

Dental drill guides are generally formed of rigid materials that constrain drill motion during a drilling procedure. However, rigid guides often do not fit properly on the teeth or fit with poor retention because teeth present complex paths of insertion and the rigid material may not deform easily to accommodate undercuts and other variations in tooth structures. There remains a need for drill guides that satisfy the concurrent constraints of high rigidity to enforce a surgical plan, high precision of fit to obtain proper alignment, and good retention to avoid slippage and rocking during use.

SUMMARY

A drill guide employs multiple layers of materials with different mechanical properties in order to achieve concurrent goals of rigidity, fit and retention. For example, a rigid exterior shell and a soft interior may be used together to securely and precisely fit a drill guide to a surgical site.

BRIEF DESCRIPTION OF THE DRAWINGS

The foregoing and other objects, features and advantages of the invention will be apparent from the following description of particular embodiments thereof, as illustrated in the accompanying drawings in which like reference characters refer to the same parts throughout the different views. The drawings are not necessarily to scale, emphasis instead being placed upon illustrating the principles of the invention.

DETAILED DESCRIPTION

Various surgical guides are described in U.S. patent application Ser. No. 12/816,710, the entire content of which is hereby incorporated by reference. Described herein are methods for fabricating such drill guides and other surgical guides using a combination of computerized planning and modeling that leads to the creation of a physical model. A final guide can then be fabricating on the physical model and a guide hole created for a drilling procedure.

As used herein, the term "axial trajectory" refers to a straight line defined by at least two separate points that characterize an intended path (typically the center of the path) for a drill into a site such as a surgical site. The axial trajectory for a particular surgical operation may be determined, for example, using planning software or the like prior to the surgical operation based upon three-dimensional data acquired from the surgical site. It will be understood that while the following description depicts lower-jaw drill guides, one of ordinary skill in the relevant art may readily adapt the surgical guides and related procedures to an upper jaw, and all such variations are intended to fall within the scope of this disclosure.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "side," "front," "back," and the like, are words of convenience and are not to be construed as limiting terms.

Figure 1:
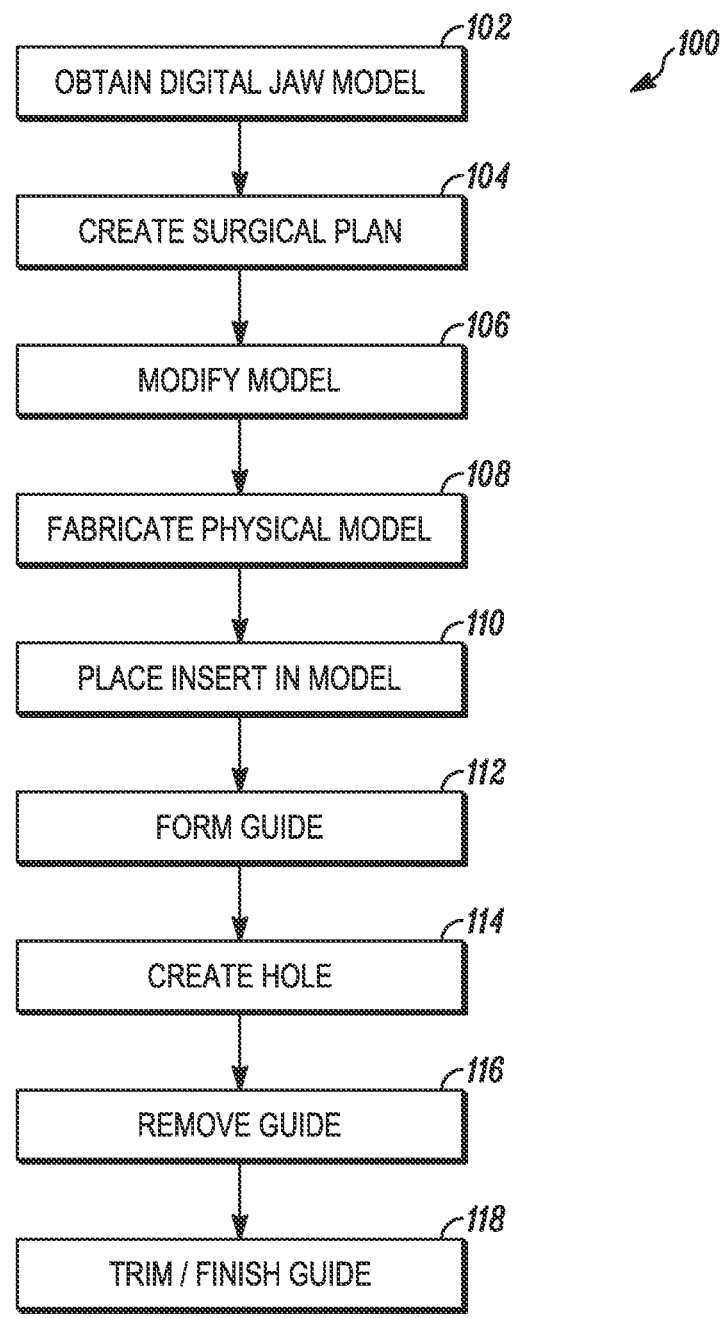
FIG. 1 shows a method for fabricating a drill guide.

FIG. 1 shows a method for fabricating a drill guide. As shown in step 102, the method 100 may include obtaining a digital jaw model of intraoral structures of a patient. The intraoral structures may include teeth, a jawbone (with or without teeth), soft tissue, existing implants and prosthetics, and so forth. This may, for example, include obtaining data based upon a Cone Beam Computed Tomography scan, a Computed Tomography scan, a laser scan, an optical scan, a Magnetic Resonance Imaging scan, an optical scan, or any other suitable scanner. It should also be understood that, depending upon the type of scanner, the data may be captured intraorally, or the data may be captured from an impression model or the like that physically captures the three-dimensional form of the intraoral structures. Thus for example, the digital jaw model may be obtained from a three-dimensional scan of a physical impression of the jaw, or the digital jaw model may be obtained from a three-dimensional scan of a physical model of the intraoral structures formed from a physical impression of the jaw.

In another aspect, multiple models may be combined to obtain the digital jaw model. For example, the method 100 may include obtaining a first digital model of the jaw for forming the guide and a second digital model for creating the surgical plan, and combining the first digital model and the second digital model to obtain the digital jaw model. The second model may include three-dimensional structure of the jaw, such as where computed tomography is used to capture an image of bone structure. Thus for example, the second model (for creating the surgical plan) may be based upon a Computed Tomography scan of the patient, a Cone Beam Computed Tomography scan of the patient, an x-ray scan. The first model may include soft tissue surrounding the jaw, such as where the scan is obtained from an optical or other external scan of the intraoral structures (either intraorally, or from an impression model or the like). The first model may include one or more teeth and any other structures present at the site of interest. Thus for example the first model may be based upon an optical scan of the intraoral structures, a three-dimensional scan of a physical impression of the intraoral structures, or a three-dimensional scan of a model formed from a physical impression of the intraoral structures.

The multiple models (e.g., first and second models) may be combined using any suitable three-dimensional modeling techniques to scale and align models from disparate sources. Suitable registration techniques are well known in the art and are not described here in detail.

As shown in step 104, the method 100 may include creating a surgical plan. This may include any computerized planning techniques such as creating the surgical plan with implant planning software, or using a suitably adaptive Computer Aided Design ("CAD") environment. In general, a surgical plan may include an axis for a dental implant that is specified relative to the digital jaw model. The surgical plan may also include a depth for a dental implant into the jaw of the patient, which information may be subsequently used to determine the depth of a corresponding cavity created in the modified digital model described below.

As shown in step 106, the method 100 may include modifying the digital jaw model to include a cavity having a predetermined orientation relative to the axis, the cavity extending into the digital jaw model. A variety of suitable techniques may be employed to create such a cavity, which may have a variety of shapes, sizes, and orientations. In general, the cavity provides an alignment feature that is ultimately used to align a hole for a drill to the axis identified during the implant planning. For example, the cavity may be formed by a cylinder centered on and parallel to the axis. The cavity may be centered on the axis.

A wide variety of possible modifications are contemplated including modifications that create recesses into the model, as well as modifications that create projections out from the model, e.g., to provide for an alignment hole off of the surface where a drilling procedure is performed. Thus in one aspect, modifying the digital jaw model may include raising a surface of the digital jaw model above the intraoral structures in an area where the axis intersects the intraoral structures, thereby providing a raised surface, and forming the cavity in the raised surface. This may include a cylindrical projection up from the surface of the intraoral structures, or any other suitably shaped and sized raised surface. The raised surface may, for example, extend to an occlusal surface of one or more adjacent teeth. The raised surface may also or instead extend about 6-12 mm above the intraoral structures, 8-10 mm above the above the intraoral structures, about 9 mm above an implant platform, or any other suitable distance. The raised surface may be perpendicular to the axis, and may provide a mating surface perpendicular to the axis for a drill stop. In one aspect, the raised surface may include (e.g., circumscribe or otherwise define by projection or the like) a cylindrical body centered on the axis. The raised surface may include a circular top or any other shape suitable for a mating surface. The height of the raised surface from the intraoral structures may be selected for a predetermined depth of an implant hole according to the surgical plan. That is, with a predetermined drill length (e.g., from a drill stop) and a predetermined implant depth, a height may be calculated for the raised surface and imposed on the modified model to obtain a drill guide that limits depth to the predetermined implant depth when using a drill with the predetermined drill length.

Thus in another aspect, the method disclosed herein may include providing a drill stop for a drill of predetermined dimensions that, when used in combination with the guide, creates a drill hole in the intraoral structures having the predetermined depth.

As shown in step 108, the method 100 may include fabricating a physical model from the digital jaw model, the physical model including a recess corresponding to the cavity of the digital jaw model. In this manner, the cavity used to capture alignment information for the implant plan is transferred to a physical model. This may include any suitable fabrication technique such as stereolithography, fused deposition modeling, selective laser sintering, polyjet printing or other similar jet printing techniques, laminated object manufacturing, computerized milling, or any other suitable additive or subtractive fabrication technique.

As shown in step 110, the method 100 may include placing an insert into the recess, the insert having an exposed top surface and an opening in the exposed top surface. The insert may provide a variety of features to support fabrication of an accurate drill guide. For example, the insert may provide a cut-resistant barrier for creation of a hole aligned to the implant plan. The insert may also add structure to a guide formed on top of the physical model, and/or may include a removable portion, e.g., a metal portion, that is retained in the drill guide to provide a tube or the like to align a drill during a drilling procedure. Several of these features and characteristics are now described in greater detail.

In one aspect, the exposed top surface may extend above the intraoral structures in an area where the axis (of the implant plan) intersects the intraoral structures. The exposed top surface may be normal to the axis of the surgical plan in order to provide a resting surface for a drill stop or the like used in a drilling procedure. The insert may be formed of a metal such as surgical stainless steel (particularly where a portion of the insert is retained in the guide during use), aluminum, or any other cut-resistant material such as a ceramic, a glass, a hard plastic, and a cut-resistant composite.

The insert may include a cylindrical tube having one or more features to mechanically engage the insert to the guide for use with the guide during a surgical procedure. In this configuration, the insert may remain in the guide (formed in step 112 below) when the guide is removed from the physical model, thus providing a tube of cut-resistant material in the guide for use when drilling.

In another aspect, the insert may be a two part insert. A bottom portion may include a post having a bottom fitted to the cavity of the physical model and a top extending above the intraoral structures. A removable top portion may include a sleeve with a cylindrical hole therethrough, wherein a bottom end of the cylindrical hole is fitted to the top of the post and a top end of the cylindrical hole provides the opening in the exposed top surface of the insert. By fashioning the sleeve to be removably and replaceably attached to the post, the sleeve can be removed with the guide for use in a drilling procedure while the bottom portion remains with the physical model. Thus the method 100 may include retaining the sleeve in the guide to guide creation of a pilot hole or a bleeding point and removing the sleeve from the guide for a subsequent drilling operation of the surgical procedure. In another aspect, the method 100 may include removing the sleeve from the guide prior to using the guide for a surgical procedure. Thus the removable sleeve may be used to provide a cut-resistant barrier for creation of a hole in the guide, while being removable from the guide prior to use. The sleeve may include one or more protuberances that mechanically engage the sleeve to the guide for use with the guide during a surgical procedure.

As shown in step 112, the method 100 may include forming a guide from a material disposed around the physical model and the insert. This may include vacuum forming a plastic sheet onto the physical model, such as a thermoplastic or a polystyrene. More generally, any thermoforming technique may be suitably employed, and term "vacuum forming" as used herein is intended to include any thermoforming process or the like unless explicitly stated to the contrary or otherwise clear from the context. The plastic may also or instead include cold-cured acrylic, light-cured acrylic, or any other suitable material or combination of materials. Forming the guide may also or instead include molding a plastic or modeling material or the like on top of the physical model with any exterior surface shape suitable for intraoral use after curing. This may for example include an impression material, or any other clay, thermoplastic, or other suitable material(s).

As shown in step 114, the method 100 may include creating a hole in the guide aligned to the opening. In general, the insert provided in step 110 may provide a cut resistant barrier for creation of the hole so that the hole is properly aligned to the implant plan. Forming the holed may include creating the hole in any suitable manner. This may for example include creating the hole with a cutting instrument such as a handheld drill, a computer controlled drill, or a drill with an alignment fixture or the like. The cutting instrument may more generally include any instrument suitable for creating a hole in the material of the guide, such as a laser, a drill, a tapered drill, a heat probe, a milling machine, a computer numerically controlled milling machine, a computer-controlled drill, a hot knife, and so forth.

As shown in step 116, the method may include removing the guide from the physical model.

As shown in step 118, the method may include trimming the guide to remove the guide from the physical model. This may include trimming the guide for use with the jaw of the patient, such as by removing excess material that would not fit within the intraoral site, or that might cause patient discomfort or otherwise interfere with proper use of the guide. More generally, this may include any suitable finishing steps such as trimming sharp and/or angular edges, sanding or otherwise smoothing corners, cleaning, and so forth.

In another aspect the method may include creating depth stop for the guide. Based upon the computerized implant plan and digital jaw model, the height of the guide can be determined. As such, a depth guide can be readily designed for a drill having a predetermined length such that the drill will go a predetermined depth into the intraoral structures when used with the guide and with the depth stop. Accordingly, the method may include providing a depth stop for the guide, the depth stop including: a cylindrical body having an outside diameter matched to the hole in the guide and an inside diameter providing an interference fit to a predetermined drill; and a flange having an outside diameter greater than the hole in the guide, the flange stopping an insertion of the predetermined drill into the hole at a predetermined depth.

Figure 2:
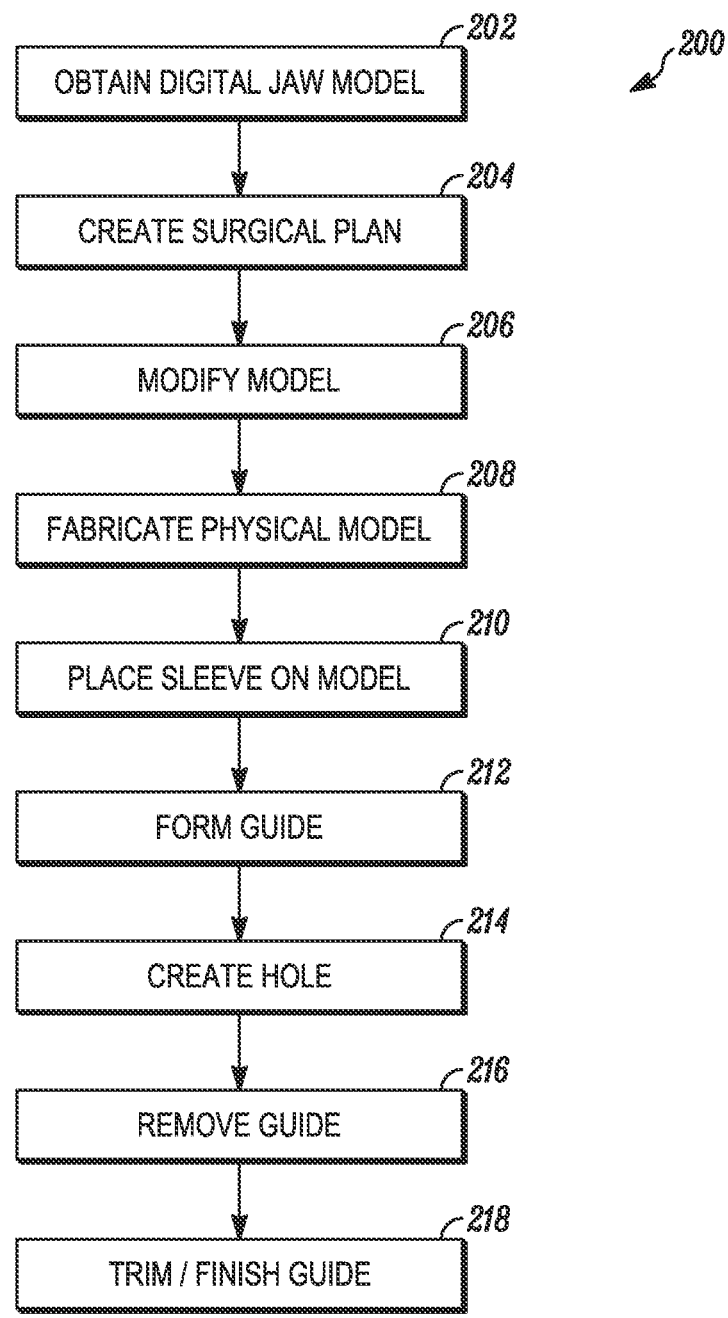
FIG. 2 shows a method for fabricating a drill guide.

FIG. 2 shows a method for fabricating a drill guide. In general, the techniques described above cover creation of a cavity in the digital jaw model to receive an insert. While the cavity described above may be placed within an elevated surface that is also added to the model, this does not cover the general case where the modifications to the digital model do not include any cavity whatsoever. Instead, the modification may include the creation of a post such as a cylinder or the like extending above the surface of the intraoral structure. Instead of an insert, a metal sleeve may then be placed around the post and used as a cut-resistant barrier during creation of a hole. Such embodiments are generally described in the method 200 below, which method includes steps similar to those described above except as specifically noted.

As shown in step 202, the method 200 may include obtaining a digital jaw model of intraoral structures of a patient.

As shown in step 204, the method 200 may include creating a surgical plan for a dental implant in the intraoral structures, the surgical plan including an axis for the dental implant, wherein the axis is specified relative to the digital jaw model.

As shown in step 206, the method 200 may include modifying the digital jaw model to include a rod extending from the intraoral structures formed by a cylinder centered on and parallel to the axis.

As shown in step 208, the method 200 may include fabricating a physical model from the digital jaw model, the physical model including a post corresponding to the rod of the digital jaw model.

As shown in step 210, the method 200 may include placing a sleeve around the post, the sleeve having an open, cylindrical interior shaped and sized to be removably and replaceably fitted to the post, and the sleeve having an exposed top surface extending above the post and an opening in the top surface formed by a top end of the open, cylindrical interior. It will be appreciated that while a cylindrical post and sleeve are convenient, simple geometries suitable for use with conventional drills, other geometries may readily be adapted to use with the systems described herein. For example, a post with a square or triangular cross section and appropriate dimensions can uniquely position a cylindrical sleeve placed thereupon.

As shown in step 212, the method 200 may include forming a guide from a material disposed around the physical model and the sleeve.

As shown in step 214, the method 200 may include creating a hole in the guide aligned to the opening.

As shown in step 216, the method 200 may include removing the guide from the physical model, which may include removing the guide and the sleeve from the physical model, or removing the guide without the sleeve from the physical model.

As shown in step 218, the method 200 may include trimming the guide to remove the guide from the physical model. This may include trimming the guide for use with the jaw of the patient.

Figure 3:
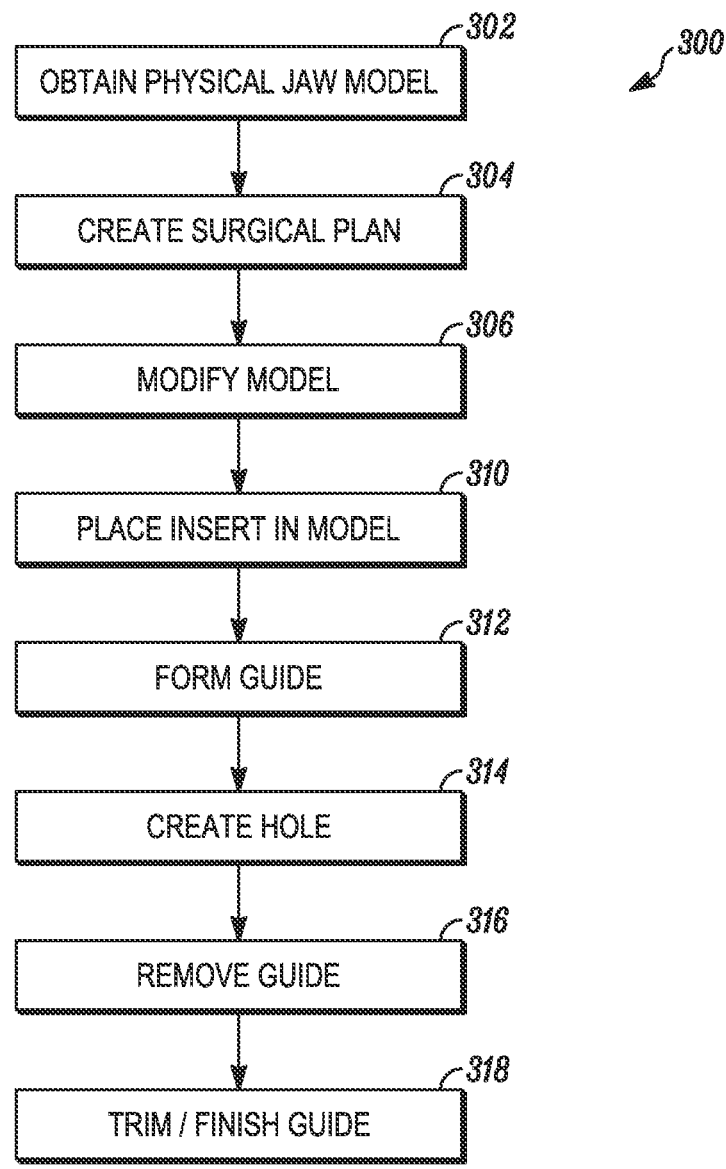
FIG. 3 shows a method for fabricating a drill guide.

FIG. 3 shows a method for fabricating a drill guide. In the following method 300, a surgical plan is transferred to a physical model rather than the digital jaw model. In this manner, the cavity may be formed after creation of the physical model using any suitable alignment jig such as drill alignment fixture or a dental drilling alignment fixture. A variety of tools for transferring computerized implant plans to physical models are commercially available and may be adapted to this application, such as the Gonyx device available from Straumann, or a variety of other dental guided surgery systems. Once the cavity of suitable depth and orientation has been created, the method 300 may in general proceed as described in the methods above.

As shown in step 302, the method 300 may begin with obtaining a physical model of intraoral structures of a patient. This may be obtained from a physical impression, or fabricated from a three-dimensional model obtained using any of the techniques noted above.

As shown in step 304, the method 300 may include creating a surgical plan for a dental implant in a jaw of the patient, the surgical plan including an axis for the dental implant.

As shown in step 306, the method 300 may include modifying the physical model to include a cavity formed by a cylinder centered on and parallel to the axis, the cavity having a depth into the physical model along the axis. This may, for example, include transferring the surgical plan to the physical model using an alignment jig. A variety of suitable alignment jigs are available in the art. This may include general dental alignment tools, dental drill alignment indicators, alignment frames, implant positioning hardware, and so forth. In general, any technique for transferring an implant plan to a physical model may be usefully employed in this context.

As shown in step 310, the method 300 may include placing an insert into the cavity, the insert having an exposed top surface and an opening in the exposed top surface. In another aspect, this step may be omitted and the guide may be fabricated using an insert-less procedure such as that described below with reference to FIG. 4.

As shown in step 312, the method 300 may include forming a guide from a material disposed around the physical model and the insert.

As shown in step 314, the method 300 may include creating a hole in the guide aligned to the opening.

As shown in step 316, the method 300 may include removing the guide from the physical model.

Figure 4:
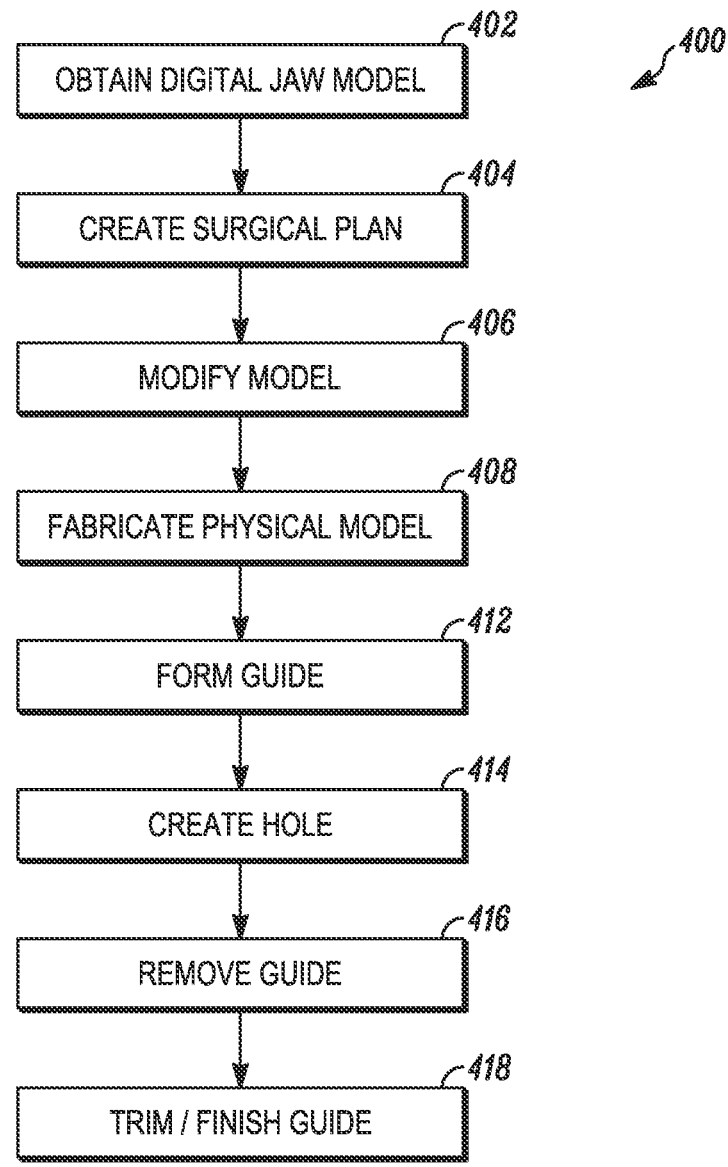
FIG. 4 shows a method for fabricating a drill guide.

FIG. 4 shows a method for fabricating a drill guide. In the embodiments above, a sleeve, insert, or other cut resistant perimeter is provided for formation of a hole in the drill guide. This may, of course be omitted, although additional care might be required in accurately forming the hole with a cutting instrument. An insert-free method is set out below, with steps being substantially as set out above except where noted.

As shown in step 402, the method 400 may include obtaining a digital jaw model of intraoral structures of a patient.

As shown in step 404, the method 400 may include creating a surgical plan for a dental implant in a jaw of the patient, the surgical plan including an axis for the dental implant, wherein the axis is specified relative to the digital jaw model.

As shown in step 406, the method 400 may include modifying the digital jaw model to include a cavity having a predetermined orientation relative to the axis, the cavity extending into the digital jaw model.

As shown in step 408, the method 400 may include fabricating a physical model from the digital jaw model, the physical model including a recess corresponding to the cavity of the digital jaw model.

As shown in step 412, the method 400 may include forming a guide from a material disposed around the physical model.

As shown in step 414, the method 400 may include creating a hole in the guide aligned to the recess. It will be noted that the hole is aligned to the recess in the physical model, and is created without the use of an insert, sleeve, or other cut-resistant guiding component.

As shown in step 416, the guide may be removed from the physical model. As shown in step 418, the guide may be trimmed and/or finished as appropriate for use in a drilling procedure.

In another aspect there is disclosed herein a guide fabricated using the techniques described above. This may, for example include a model of one or more intraoral structures, the model modified to include a retaining feature to removably retain an object; a sleeve removably held in position relative to the model by the retaining feature; and a guide vacuum formed to the shape of the one or more intraoral structures and the sleeve, wherein the sleeve is retained captive in the guide and removable with the guide from the model.

Figure 5:
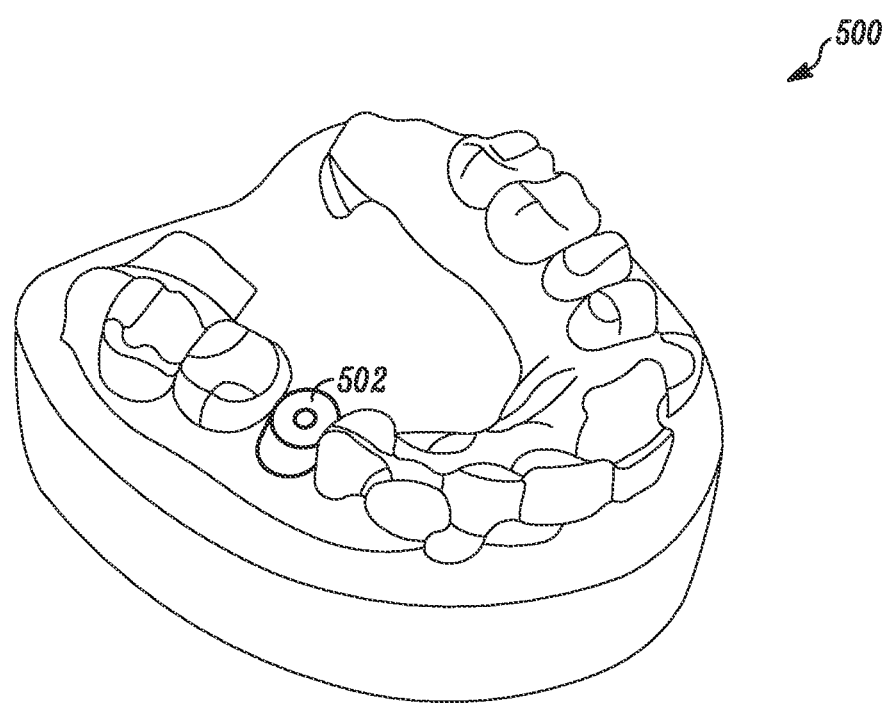
FIG. 5 shows a modified digital model, or a physical model fabricated from same.

FIG. 5 shows a modified digital model, or a physical model fabricated from same. The model 500 may be modified as described above to include a raised surface 502, e.g., a raised cylinder with a hole on a top surface thereof. A guide formed around this model will include a hole off of the surface of the surrounding intraoral structures that is aligned to the implant plan.

Figure 6:
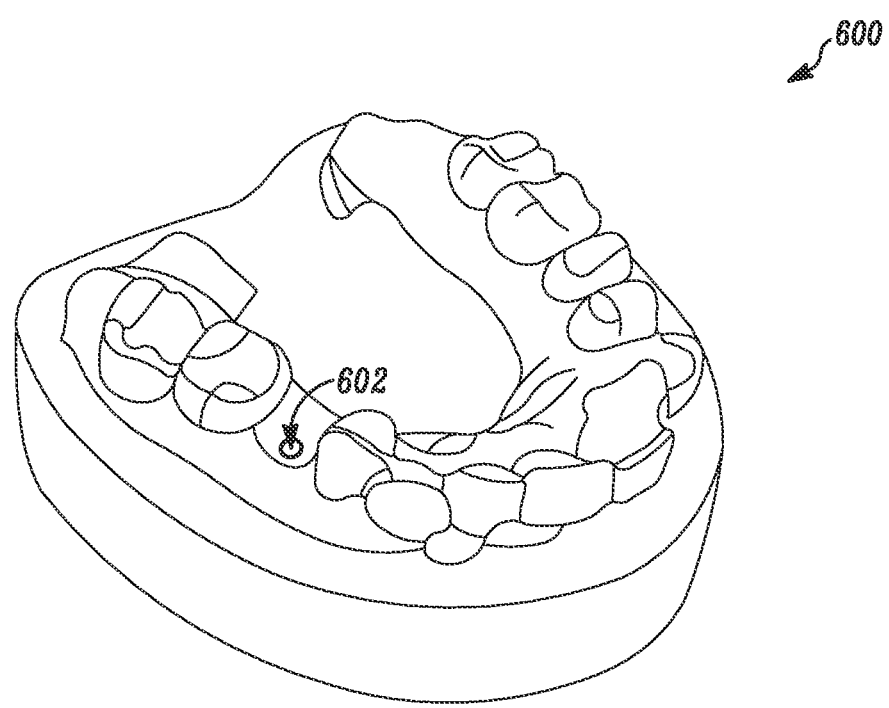
FIG. 6 shows a modified digital model, or a physical model fabricated from same.

FIG. 6 shows a modified digital model, or a physical model fabricated from same. The model 600 may be modified to include a recess 602 or cavity into which an insert can be placed for creation of a guide as described above.

Figure 7:
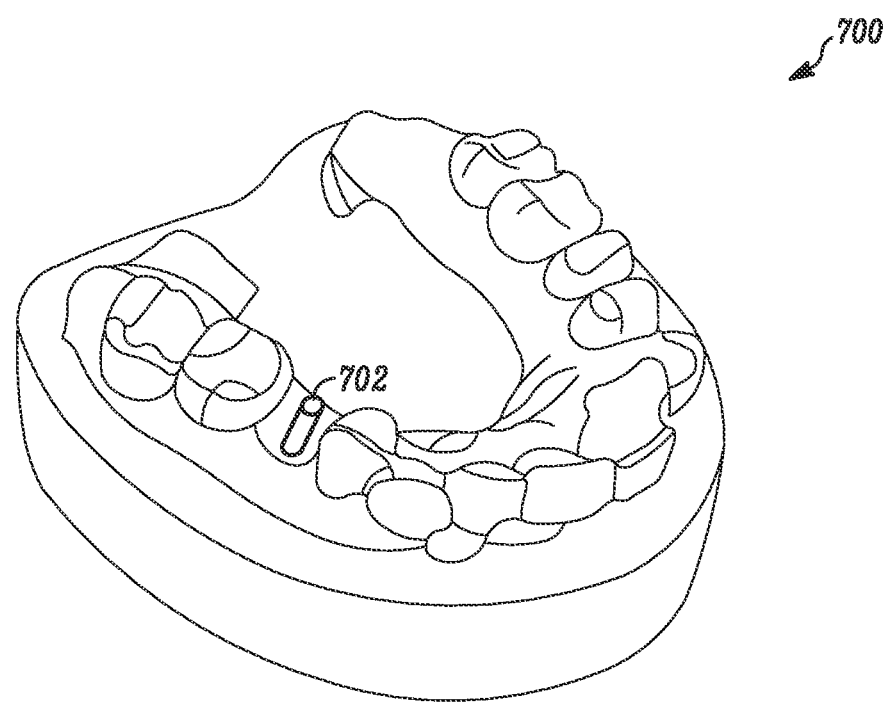
FIG. 7 shows a modified digital model, or a physical model fabricated from same.

FIG. 7 shows a modified digital model, or a physical model fabricated from same. The model 700 may be modified to include a post 702 onto which a sleeve can be placed for creation of a guide as described above. In some implementations, the sleeve may be captured by the guide (e.g., via adhesive or other means), so as to form a guide tube to further guide a drill.

Figure 8:
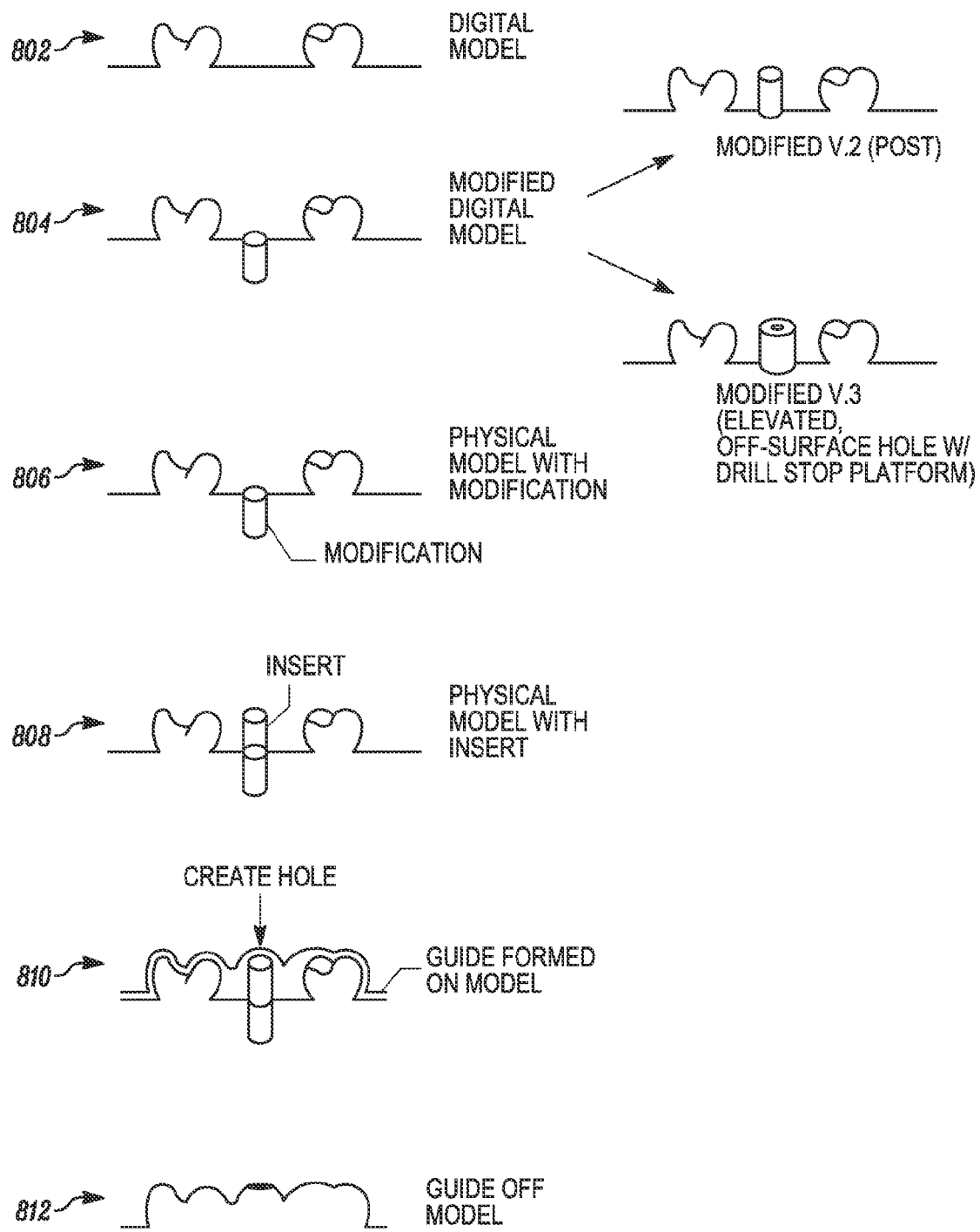
FIG. 8 illustrates steps to a method for fabricating a guide.

FIG. 8 illustrates steps to a method for fabricating a guide.

In a first step 802, a digital model of a surgical site may be provided including, e.g., dentition, soft tissue, bone, and so forth.

In a second step 804, the digital model may be modified using the various techniques described above to provide a modified digital model. For example, a cylindrical opening may be created in dentition and/or jaw around a desired trajectory for a drill. In another aspect, a cylindrical post or the like may be created extending upward from the dentition and/or jaw around the desired trajectory. In another aspect, a cylindrical post may be created that includes a hole centered in the cylinder. This later configuration creates a hole that is used to create a guiding hole for a drill, along with a drill stop formed from the flat, top surface of the cylinder to guide a drill.

In a third step 806, a physical model may be fabricated based on the modified digital model using, e.g., any suitable fabrication technique such as stereolithography, fused deposition modeling, CNC milling, and so forth.

In a fourth step 808, any suitable insert or combination of inserts may be added to the model. For example, in the first embodiment noted above (cylindrical hole in jaw), a post or similar insert may be placed into the hole to form a shape around which a guide may be formed.

In a fifth step 810, a guide may be formed around the physical model and insert using, e.g., vacuum forming or any other suitable technique for created an model formed to the surface of the physical model.

In a sixth step 812, the guide may be removed from the physical model for use in a drilling procedure. Any suitable finishing steps may be performed on the guide, such as trimming, test-fitting, and so forth.

Figure 9:
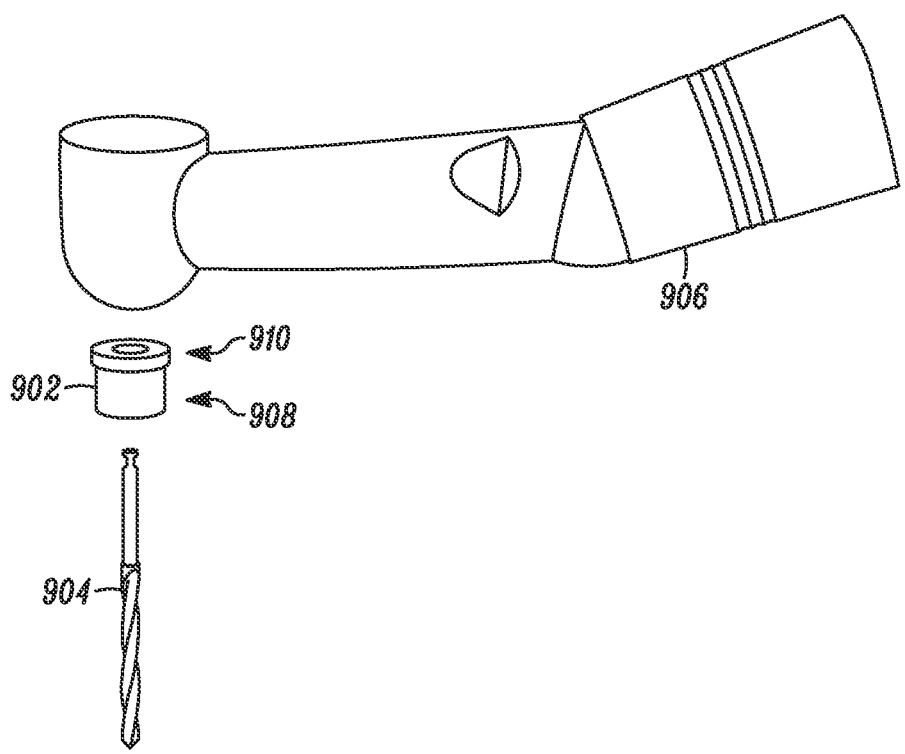
FIG. 9 shows a dental drill with a drill stop.

FIG. 9 shows a dental drill with a drill stop. As noted above, a drill stop 902 may be used with a drill bit 904 of predetermined length and diameter to control the use of a dental drill 906 or the like in a drilling procedure. The drill stop may have a lower section 908 with a diameter fitted to a drill guide, and an upper portion 910 with a flange or the like that is too large to pass through the drill guide. Thus the drill stop can provide centering of a drill, while also controlling a depth of drilling by preventing an incursion of the assembled drill, drill bit, and drill stop beyond a predetermined depth into the guide. Furthermore, with parameters such as an implant depth, a series of drill stops may be provided for a series of drill bits with increasing diameter. If the drill stops have a similar outside diameter, then they can be used in sequence with a single drill guide in order to create progressively larger diameter holes centered on a trajectory for an implant plan.

Figure 10A:
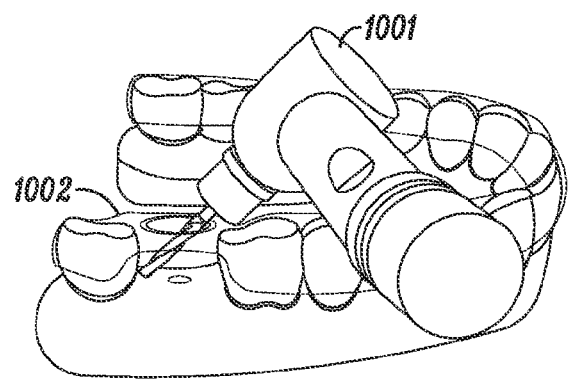
FIGS. 10A-10C illustrate steps of a technique for using a drill stop.
Figure 10B:
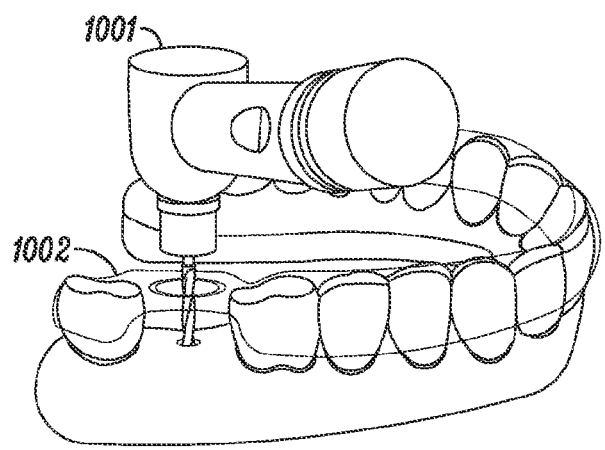
Figure 10C:
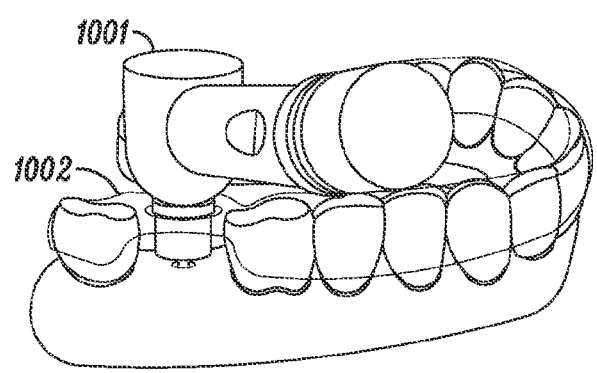

FIG. 10 (in FIGS. 10A-10C) illustrates steps of a technique for using a drill stop. As shown in FIG. 10A, a drill 1001 with a drill bit and a drill stop as described above may be inserted into a drill guide 1002 off-axis from the trajectory of an implant plan. The drill guide 1002 may, for example, include any of the guides fabricated as described above. In some implementations, the path of the drill bit is further constrained by a guide tube (FIG. 13), which keeps the drill bit on-axis. As shown in FIG. 10B, the drill bit may then be manually aligned to the trajectory and/or the top of a preexisting pilot hole. As shown in FIG. 10C, drilling may begin. As the drill bit moves into the drilling site, the drill stop can center the drill to the trajectory and, at a predetermined depth, stop the drill bit from further incursion into the drilling site. The drill may then be removed and the drill bit may be replaced with a larger diameter drill bit and a corresponding drill stop for drilling a larger hole.

It will be further appreciated that, while a tooth-supported guide is illustrated in FIG. 10, the principles disclosed herein may be suitably adapted for use with an endentulous guide that rests on the gingiva and/or gum and/or bone and is secured with one or more bone screws.

Figure 11:
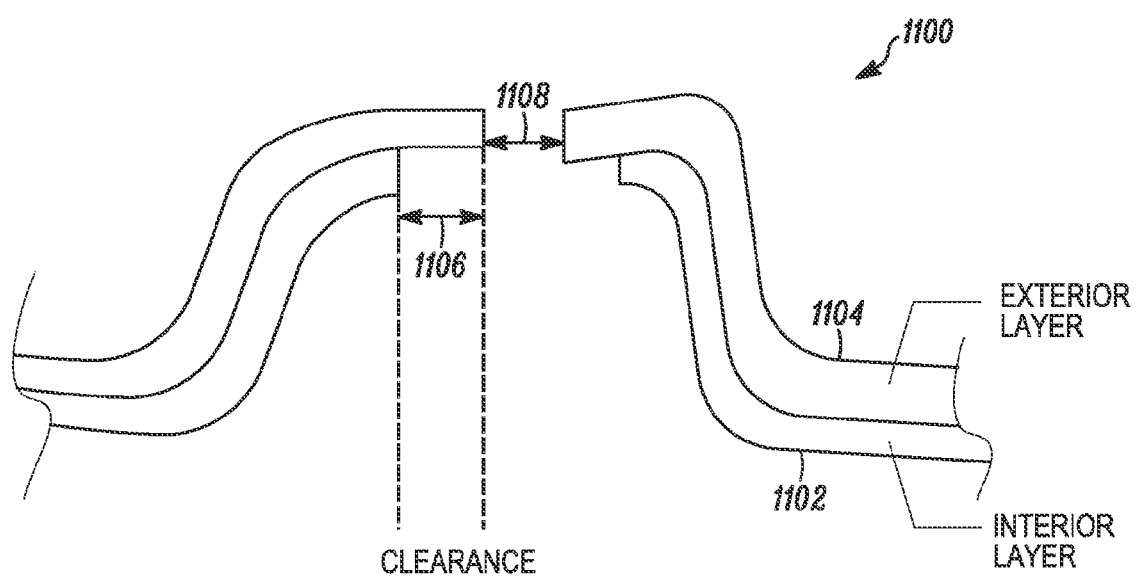
FIG. 11 shows a multi-layer guide.

FIG. 11 shows a multi-layer guide. It may be difficult to manufacture a drill guide which fits the dentition securely and precisely with adequate retention. One challenge is the presence of undercuts in the anatomy of the teeth of varying severity, which are positioned at differing angles to each other. The difficulties in achieving a secure, tight fit to dentition may be addressed in part by providing a guide 1100 with multiple layers including a first layer 1102 serving as an interior (e.g., tooth-facing) surface that is pliable and compressible, along with a second layer 1104 that provides an exterior (e.g., facing away from tooth surfaces) surface that is sufficiently rigid to enforce a planned drill trajectory. In general, the first layer 1102 may include a clearance 1106 away from a hole 1108 for a drill. In general, the clearance 1106 permits the pliable material of the first layer 1102 to avoid contact with a drill that is guided by the hole 1108 in the more rigid second layer 1104, thus preventing the material from the first layer 1102 from becoming bound in the drill and entering a surgical site.

Accordingly, in one aspect the methods contemplated herein may include forming a clearance in the first layer 1102 to provide a second hole about the axis of a drill trajectory, where the second layer has a greater diameter than a corresponding hole 1108 in the second layer 1104.

It will be understood that terms such as pliable and rigid are somewhat relative. As used in this context, the term "rigid" or "substantially rigid" is intended to mean sufficiently rigid to maintain a position of a drill during a drilling procedure as contemplated herein, and adequate rigidity will be readily understood and appreciated by one of ordinary skill in the art. Similarly, the term "pliable" or "substantially pliable" is intended to mean sufficiently soft, pliable, and/or compressible to variably fill a space between a rigid drill guide and dentition by yielding to the dentition and, when compressed, retaining the relative position of the guide to the dentition with sufficient fidelity for the guide to function adequately. Where precise values for hardness or stiffness are not given, it will be understood that these terms at least convey a relative difference in such mechanical properties. Thus, rigid may be understood to mean more rigid, and pliable may be understood the mean less rigid. Again, suitable physical properties will be readily understood by one of ordinary skill in the art, and exemplary values may be ascertained, for example, from the example materials described below.

Figure 12:
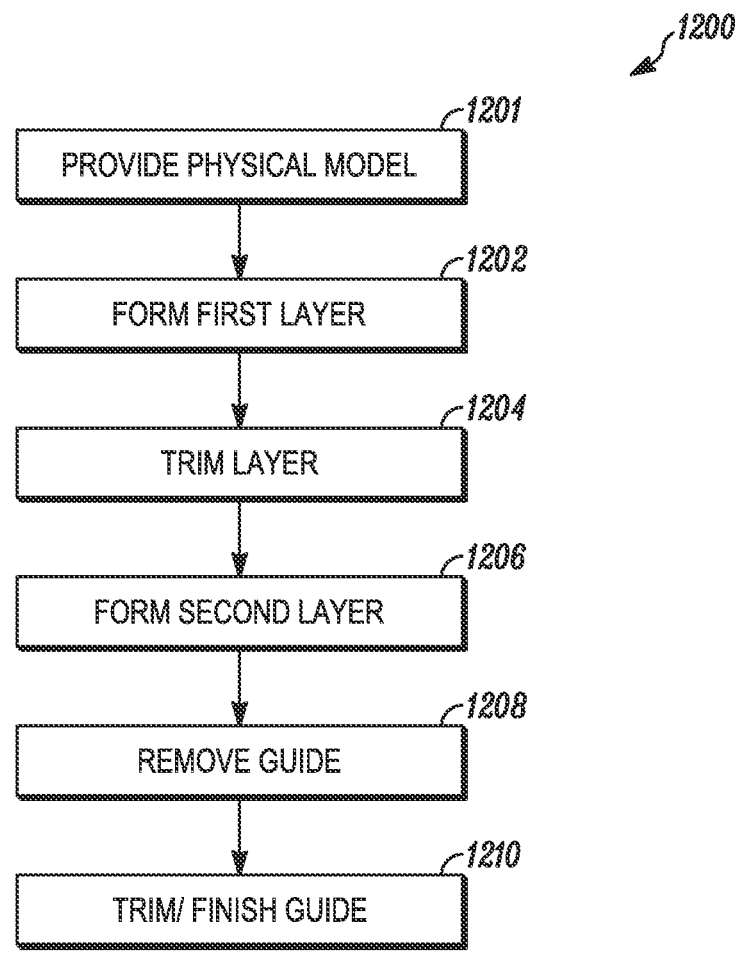
FIG. 12 shows a method for fabricating a multi-layer drill guide.

FIG. 12 shows a method for fabricating a multi-layer drill guide. In one aspect, a multi-layer vacuum forming technique may be employed to obtain a drill guide superior gripping and stability when placed for use from a combination of a rigid exterior layer and a pliable interior layer, which multiple layers may be formed, e.g., from a number of vacuum-forming operations or any other suitable fabrication techniques. It will be noted that terms such as a first layer and a second layer are used below as terms of convenience, and not to require or suggest a particular order in which the layers are formed unless expressly stated to the contrary. More generally, it should be clear from the various embodiments described herein that a rigid layer may be formed before a pliable layer or a pliable layer may be formed before a rigid layer.

As shown in step 1201, the method may begin with providing a physical model. This may include any of the physical models described above which may be based on modified digital models of intraoral structures such as dentition and surrounding tissue for a patient. As described above, the modified digital model may include a feature aligned to an axis for a dental implant, and the physical model fabricated from the modified digital model may also include the feature (or more precisely, a physical instantiation of the feature, although the term is used interchangeably herein to refer to the digital or physical version of the feature). The feature may generally be a cavity, a post, or any other physical feature described that might represent the intended axis (and corresponding drill trajectory) for the implant.

It will be appreciated that a physical model of one or more intraoral structures may be fabricated from any corresponding digital jaw model that is available for a patient, or the physical model may be obtained directly from a patient using a physical molding or casting technique. It will also be appreciated that the physical model may be useful for certain fabrication steps such as vacuum forming as described below. However, in other aspects, the physical model may be omitted entirely, and various layers of a multi-layer guide may be fabricated directly from a digital model using any suitable rapid prototyping technology such as the various rapid prototyping technologies described herein.

As shown in step 1202, the method may include fabricating a first layer of a pliable material to serve as an underlayer that flexibly conforms to a tooth surface or the like. A model of dentition including a rod indicating the implant position (all as described above) may be used as a model for fabricating the drill guide. Undercuts in the model may be blocked out by filling the undercuts with dental blockout compound (e.g., FILL-IT, a compound made available by AMERICAN DENTAL SUPPLY, INC.), or any other suitable material. A relatively soft, resilient material such as Proform soft ethylene vinyl acetate (EVA) vacuum forming material (0.040" thick) commercially available from TruTain Orthodontics and Dental Supplies or any similar material may be suitably used as the first layer, and may be formed onto the model by vacuum forming.

Alternatively, step 1202 may include forming a first layer from a rigid material. The rigid material may be formed into a shell such as any of the thin-layered or other shapes and forms described above with an interior surface corresponding to one or more intraoral structures of a patient's mouth. For example, the rigid material may be a thermoplastic or other material that can be placed into a pliable state through the application of heat, light or other stimuli. In this pliable state, the rigid material may be disposed onto a physical jaw model and then returned to a rigid state (e.g., through cooling). As another example, the rigid material may be a light-curable, heat-curable, air curable or otherwise curable material that can be disposed onto a physical model and then cured into a rigid form.

In another aspect, the method 1200 may include forming the first layer by fabricating the first layer directly from the rigid material with a rapid prototyping system based upon a digital jaw model.

As shown in step 1204, the method 1200 may include trimming the layer. To accomplish this, the first layer of material may be removed from the model and trimmed to extend to the gingival margin of the teeth. The material may be further trimmed to cover all teeth except the tooth (or teeth) adjacent to the surgical site. More specifically, the material may be trimmed to provide a clearance as described above relative to the drilling trajectory and the drill bit that will be used for drilling. Any suitable setback (shown as a "clearance" in FIG. 11) may be employed provided that there is sufficient space to avoid interference of the soft material with a drilling, while covering a sufficient area of dentition (e.g., other teeth) to provide a stable support for the drill guide. This may, for example be one millimeter, five millimeters, or any other suitable setback. A larger setback of any suitable size may preferably be employed to ensure clearance from a drill, provided the first layer covers sufficient areas of the surrounding dentition to provide substantial coverage of tooth support regions.

As shown in step 1206, a second layer may be formed on the first layer. To perform this step, the trimmed first layer may be returned to a physical model in order to provide rigid support for additional vacuum-forming. Thus the trimmed soft EVA material may be placed onto the model and a second layer may be formed on top of the first layer. The second layer may be formed of any suitably rigid plastic or other material(s) such as acrylonitrile butadiene styrene ("ABS") or polystyrene. As noted above, a variety of different types of guides may be formed. Thus the step 1206 of forming the second layer may optionally include adding a guide tube, adding an insert such as a post or guide ring, and so forth, prior to forming the second layer. A material such as Tru-Tain Splint vacuum forming material (0.040" thick) or any other suitably rigid material may be vacuum formed onto the model overlaying and laminating the soft EVA underlayer. In some implementations, the guide tube may be captured by the vacuum formed material, thereby being included in the manufactured drill guide. In some implementations, the guide tube need not be captured by the vacuum formed material.

In another aspect where a rigid layer is initially formed with an interior surface shaped to intraoral structures, step 1206 may include forming the second layer of a pliable material on the interior surface. This may, for example, include depositing the pliable material onto the interior of the first layer, such as by painting or otherwise disposing the pliable material onto the interior surface, or by dipping the rigid layer into a liquid bath of the pliable material. The pliable material may then be cured using any suitable curing or drying technique. It will be noted that while two layers are described, any number of intermediate layers may also or instead be employed. For example, where the rigid material is dip-coated in a bath of the pliable material, the resulting drill guide may include a top and bottom layer of pliable material, with a rigid material encased therebetween. It will also be understood that sacrificial layers of material may be usefully employed during processing. For example, a physical model may be painted with a spacer to provide room for a coating of pliable material when a rigid material is formed on the physical model. The space may remain with the physical model when the rigid material is removed, and the resulting impression in the rigid material will be slightly enlarged, and may accommodate a pliable material disposed therein.

In another aspect, the method 1200 may be adapted for use with direct three-dimensional printing of the guide. For example, the modified digital model described in step 1201 may be further processed to create a model of a guide conforming to the digital model of the jaw, and the first and second layers may be further created as separate digital models for direct fabrication. In step 1202 the first layer may then be fabricated directly from a pliable material (either including the hole, or with the hole added in a separate fabrication step prior to adding the second layer). Then, the trimming step may be omitted, and the second layer may be added in step 1206 by directly fabricating the second layer (with a second hole that has a diameter less than the hole in the first layer) directly on top of the first layer. In this manner, the guide may advantageously be directly fabricated without any intermediate steps of fabricating a physical jaw model or trimming the hole in the first layer to provide clearance for a drill during use. A variety of three-dimensional printing techniques may be suitably adapted to this technique, or similar techniques adapted to the capabilities of various three-dimensional fabrication technologies. All such variations as would be apparent to one of ordinary skill in the art are intended to fall within the scope of this disclosure.

In another aspect, a composite vacuum-forming material may be used. For example, multi-ply vacuum-forming materials are commercially available with a polystyrene surface and an EVA surface pre-laminated together. While this may restrict a user's flexibility in terms of types and thicknesses of materials, some of these commercially available laminates may be suitable for use in fabricating a multi-layer guide as contemplated herein.

As shown in step 1208, the completed, composite, multi-layer guide may be removed from the model.

As shown in step 1210, the guide may be trimmed or otherwise finished for use as a dental guide. In one aspect, this may include forming a hole in the first layer and the second layer aligned to the axis of a dental implant for which a hole is to be drilled using the guide. While this is illustrated as a final or ending step in a process, it will be understood that the hole may be created at any time during fabrication of the guide, and may include two separate and independent steps of creating a first hole in the first layer and a second hole in the second layer. In another aspect, where a layer is directly fabricated from a rapid prototyping system, a source digital model may include an appropriately positioned hole and the layer may be fabricated with the hole already present in the desired location. In another aspect, where a physical model is adapted to create a corresponding feature, the hole may be created when the first layer is formed onto the physical model. Thus a variety of techniques are generally contemplated for creating a hole for use in a drill guide as contemplated herein, any of which may be used alone or in combination to create suitable holes in the first layer and second layer.

In one aspect, a laminate of soft EVA is thus formed as depicted in FIG. 11. The material may be trimmed to the extent of the gingival margin and the plastic overlaying the guide tube may be trimmed to create a guide hole. The drill guide may then be removed from the model and the perimeter trimmed to a length consistent with appropriate retention on the plastic model and on the stone model of the patient's dentition. It should be noted that the resulting guide has numerous advantages that may not be readily apparent. For example, when the rigid material is vacuum formed over the pliable material, the vacuum forming process slightly compresses the pliable material around the shape of the teeth, and when the guide is removed from the physical model, the interior shape of the pliable material becomes slightly smaller in volume than the model as the pliable material elastically expands to its resting state. As a result, when the guide is placed in a patient's mouth, the pliable material compresses somewhat within the rigid shell to form a tighter, more uniform fit to the teeth which, in practice, has been demonstrated to be significantly more stable than a rigid shell alone, and well suited to use as a drill guide.

In another aspect, the multi-layer model may be fabricated using, e.g., a rapid prototyping technology such as multi jet or polyjet printing, stereolithography, selective laser sintering, fused deposition modeling, computerized milling, and so forth. In particular, where such a fabrication platform has multi-material capabilities, a model corresponding to the design described above may be created in a three-dimensional modeling environment, and the model may be fabricated using a relatively soft, compressible material as the interior layer and a relatively rigid material as the exterior layer, as described above. Similarly, the interior layer may be fabricated using a rapid prototyping technology based on a digital model of the patient's dentition, and the rigid exterior layer may be vacuum formed on to the interior layer. Any such combinations of fabrication techniques for obtaining the model shown in FIG. 11 may be suitably employed. In these contexts, the digital model of the teeth may be made slightly smaller in overall shape and volume so that the pliable layer can compress within the rigid layer to provide a more secure bond to tooth structures and, as a result, a more stable drill guide.

In general, the various techniques for fabricating drill guides as described above may employ rapid prototyping techniques in various combinations. Thus each physical model (modified or otherwise), each drill guide layer, and each drill stop, as well as subcomponents or subassemblies of the foregoing, may be fabricated using rapid prototyping. By way of non-limiting example, a pole may be fabricated into a tooth model, or as a part that fits into a hole in a tooth model, using a three-dimensional printer. In general, the pole serves to align a guide hole to an intended trajectory. A platform, which may also be printed, may have a generally annular shape that fits around the pole and establishes a height for a tube that fits over the pole. In this manner, the tube may be positioned to control drill depth based upon the thickness of the platform.

Figure 13:
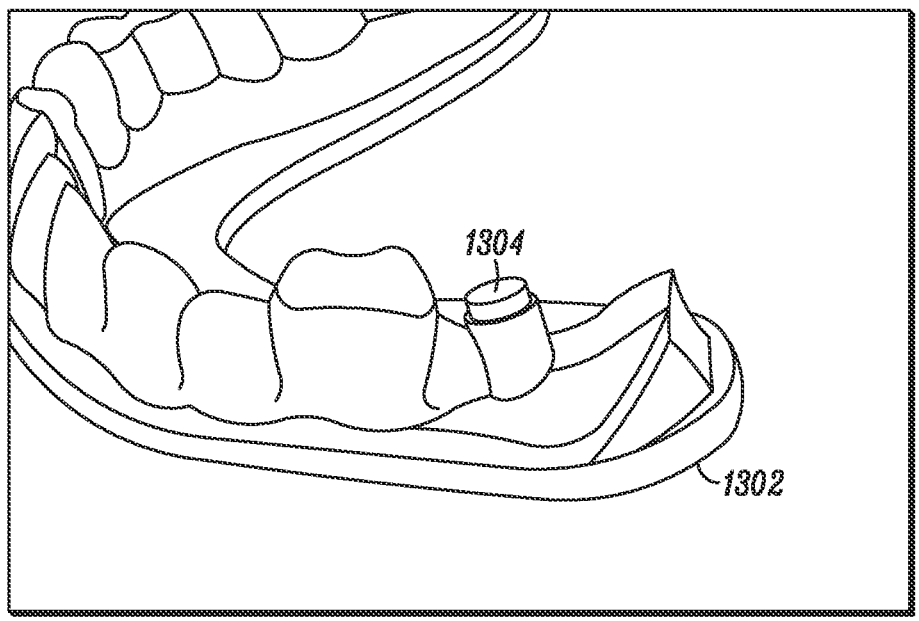
FIG. 13 shows a physical model with a post.
Figure 14:
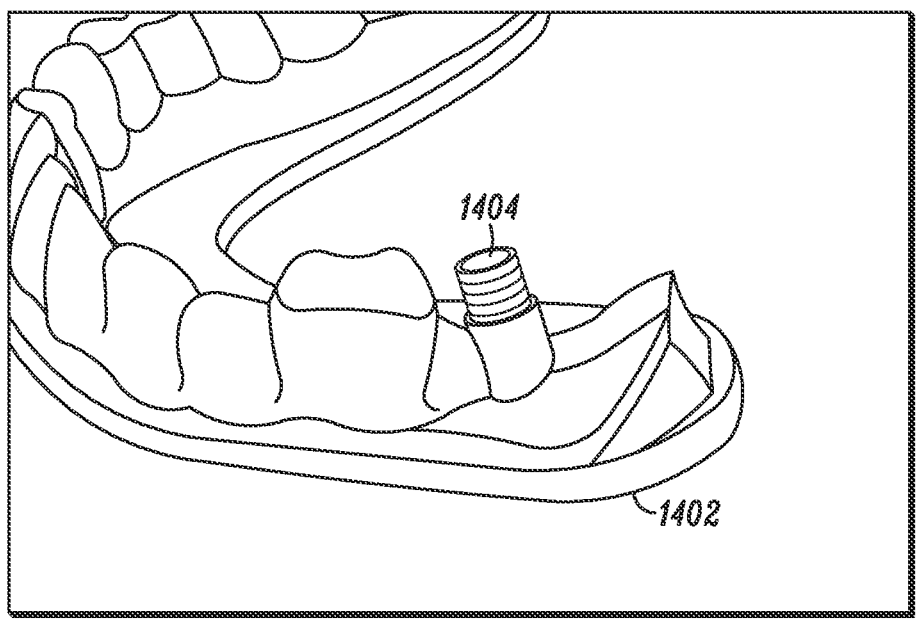
FIG. 14 shows a physical model with a guide tube placed over a post.

FIG. 13 shows an exemplary physical model 1302 of a modified digital model that includes a post 1304 to secure a guide tube. FIG. 14 show the physical model 1402 with a guide tube 1404 (such as a metal tube) placed over the post. As discussed above, a guide may be vacuum formed over the model and tube so that the tube is captured within the guide to provide a metal guiding tube in the resulting drill guide.

It will be appreciated that many of the above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as the various systems described above, or all of the functionality may be integrated into a dedicated, standalone device. All such permutations and combinations are intended to fall within the scope of the present disclosure.

In other embodiments, disclosed herein are computer program products comprising computer-executable code or computer-usable code that, when executing on one or more computing devices (such as the devices/systems described above), performs any and/or all of the steps described above. The code may be stored in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the processes described above may be embodied in any suitable transmission or propagation medium carrying the computer-executable code described above and/or any inputs or outputs from same.

It will be appreciated that the methods and systems described above are set forth by way of example and not of limitation. Numerous variations, additions, omissions, and other modifications will be apparent to one of ordinary skill in the art. Thus, for example, while dental implant procedures are clearly contemplated, this disclosure is not limited to oral surgery, but may facilitate any osteotomy, bone surgery, bone replacement, or other surgical procedure requiring drilling into bone or hard tissue, or more generally any procedure involving alignment of a tool to a desired trajectory. In addition, the order or presentation of method steps in the description and drawings above is not intended to require this order of performing the recited steps unless a particular order is expressly required or otherwise clear from the context.

It should further be appreciated that unless expressly stated to the contrary or otherwise clear from the context, each method step recited herein is intended to include causing that step to be performed by an external resource controlled by the disclosed method. Thus for example a step such as fabricating a physical model includes causing the physical model to be fabricated, e.g., by transmitting a digital model to a fabrication resource such as any of the prototyping systems described herein.

While particular embodiments of the present invention have been shown and described, it will be apparent to those skilled in the art that various changes and modifications in form and details may be made therein without departing from the spirit and scope of the invention as defined by the following claims. The claims that follow are intended to include all such variations and modifications that might fall within their scope, and should be interpreted in the broadest sense allowable by law.

What is claimed is:

1. A method for fabricating a drill guide comprising:
obtaining a digital jaw model of one or more intraoral structures of a patient;
creating a surgical plan for a dental implant in a jaw of the patient, the surgical plan including an axis for the dental implant, wherein the axis is specified relative to the digital jaw model;
creating a physical jaw model of the one or more intraoral structures, the physical jaw model including a feature aligned to the axis for the dental implant;
vacuum forming a first layer of a pliable material onto the physical jaw model;
vacuum forming a second layer of a rigid material onto the first layer; and
forming a hole in the first layer and the second layer aligned to the axis of the dental implant based on the feature in the physical model.

2. The method of claim 1 wherein the rigid material is a thermoplastic material.

3. The method of claim 1 further comprising forming a clearance in the first layer to provide a second hole about the axis in the first layer having a greater diameter than the hole in the second layer.

4. The method of claim 1 wherein creating the physical jaw model includes creating the physical jaw model with a rapid prototyping system based upon the digital jaw model.

5. The method of claim 4 wherein the rapid prototyping system includes a stereolithography system.

6. The method of claim 4 wherein the rapid prototyping system includes a computerized milling system.

7. The method of claim 4 wherein the rapid prototyping system includes one or more of a fused deposition modeling system, a selective laser sintering system, and a polyjet printing system.

8. The method of claim 1 wherein the first layer includes ethylene vinyl acetate.

9. The method of claim 1 wherein the second layer includes polystyrene.

10. The method of claim 1 further comprising obtaining the digital jaw model from a scan of the patient.

11. The method of claim 10 wherein the digital jaw model is based upon one or more of a Computed Tomography scan, a Cone Beam Computed Tomography scan, and an x-ray scan, and a Magnetic Resonance Imaging scan.

12. The method of claim 10 wherein the digital jaw model is based upon one or more of an optical scan and a laser scan.

13. The method of claim 1 further comprising obtaining the digital jaw model from a physical impression of the jaw of the patient.

14. The method of claim 1 wherein the second layer includes acrylonitrile butadiene styrene.

15. The method of claim 14 wherein the multi-ply vacuum-forming material includes a polystyrene surface and an ethylene vinyl acetate surface pre-laminated together.

16. The method of claim 1 wherein the first layer is provided for vacuum forming with a thickness of about 0.040 inches.

17. The method of claim 1 wherein the second layer is provided for vacuum forming with a thickness of about 0.040 inches.

18. The method of claim 1 wherein the first layer and the second layer are combined as a multi-ply vacuum-forming material.

19. The method of claim 1 wherein the feature of the physical jaw model aligned to the axis for the dental implant includes a post.

20. The method of claim 1 wherein the feature of the physical jaw model aligned to the axis for the dental implant includes a cavity.

* * * * *